(12) United States Patent
Ohno (10) Patent No.: US 9,655,570 B2
(45) Date of Patent: May 23, 2017

(54) RADIOLOGICAL IMAGE PROCESSING APPARATUS AND RADIOLOGICAL IMAGE PROCESSING PROGRAM

(75) Inventor: Yoshinori Ohno, Kyoto (JP)

(73) Assignee: SHIMADZU COPORATION, Kyoto (JP)

(*) Notice: Subject to any disclaimer, the term of this patent is extended or adjusted under 35 U.S.C. 154(b) by 1785 days.

(21) Appl. No.: 12/680,773

(22) PCT Filed: Oct. 2, 2007

(86) PCT No.: PCT/JP2007/069262
§ 371 (c)(1),
(2), (4) Date: Mar. 30, 2010

(87) PCT Pub. No.: WO2009/044452
PCT Pub. Date: Apr. 9, 2009

(65) Prior Publication Data
US 2010/0215243 A1 Aug. 26, 2010

(51) Int. Cl.
*G06K 9/00* (2006.01)
*A61B 6/06* (2006.01)
(Continued)

(52) U.S. Cl.
CPC .............. *A61B 6/06* (2013.01); *A61B 6/4035* (2013.01); *A61B 6/4291* (2013.01);
(Continued)

(58) Field of Classification Search
CPC ............. G06T 5/10; G06T 2207/10116; G06T 2207/20224
(Continued)

(56) References Cited

U.S. PATENT DOCUMENTS 6,269,176 B1 * 7/2001 Barski et al. ................ 382/128
6,333,990 B1 * 12/2001 Yazici et al. ................ 382/132
(Continued)

FOREIGN PATENT DOCUMENTS

JP          2507659 B2      4/1996
JP       2002-325755 A     11/2002
(Continued)

OTHER PUBLICATIONS

Mitchell, J. G. (1978). Studies in the development of equipment for improving resolution in nuclear medicine imaging (Order No. U442593). Available from ProQuest Dissertations & Theses Global: Health & Medicine. (301378394). Retrieved from https://search.proquest.com/docview/301378394?accountid=14753.*
International Search Report for the Application No. PCT/JP2007/069262 mailed Nov. 13, 2007.

*Primary Examiner* — Mark Holcomb
(74) *Attorney, Agent, or Firm* — Cheng Law Group, PLLC (57) ABSTRACT

A radiological image processing apparatus of this invention includes a separating device, an adjusting device and a removing device. Since a corrected image is generated using the radiological image taken through an object under examination, each image can be acquired by one radiographic operation without acquiring data for grid correction beforehand. The radiological image taken through the object is separated into a grid image and a non-grid image, and a corrected image is generated by adjusting intensity of the grid image on real space based on the non-grid image. Thus a high-precision correcting process is realized by one radiographic operation.

10 Claims, 4 Drawing Sheets

(51) Int. Cl.
*A61B 6/00* (2006.01)
*G06T 5/00* (2006.01)
*G06T 5/10* (2006.01)

(52) U.S. Cl.
CPC .......... *A61B 6/5252* (2013.01); *A61B 6/5282* (2013.01); *A61B 6/583* (2013.01); *A61B 6/585* (2013.01); *G06T 5/002* (2013.01); *G06T 5/10* (2013.01); *G06T 2207/10116* (2013.01); *G06T 2207/20224* (2013.01)

(58) Field of Classification Search
USPC .... 378/28–33, 44–50, 51, 62; 382/128, 130, 382/132
See application file for complete search history.

(56) References Cited

U.S. PATENT DOCUMENTS

| | | | |
|---|---|---|---|
| 7,039,151 B2 * | 5/2006 | Tsujii | 378/7 |
| 7,142,705 B2 * | 11/2006 | Inoue et al. | 382/132 |
| 7,474,774 B2 * | 1/2009 | Inoue | 382/128 |
| 2003/0016854 A1 | 1/2003 | Inoue et al. | |

FOREIGN PATENT DOCUMENTS

| | | | |
|---|---|---|---|
| JP | 2002-330343 A | 11/2002 | |
| JP | 2002-330344 A | 11/2002 | |
| JP | 2003-260053 A | 9/2003 | |
| JP | 2004-344670 A | 12/2004 | |
| JP | 2005-324069 A | 11/2005 | |

* cited by examiner

RADIOLOGICAL IMAGE PROCESSING APPARATUS AND RADIOLOGICAL IMAGE PROCESSING PROGRAM

TECHNICAL FIELD

This invention relates to a radiological image processing apparatus and a radiological image processing program for processing radiological images taken through a grid for removing scattered radiation.

BACKGROUND ART

A radiological image processing apparatus accumulates radiation energy transmitted through an object under examination, in an image sensor called "flat panel radiation detector (FPD: Flat Panel Detector)", and converts it into electric signals for visualization. At this time, the FPD accumulates linear radiation energy transmitted through the object, but at the same time accumulates also low-energy radiation scattered about when transmitted through the object. Consequently, image quality will be lowered, such that the contrast of the radiological image taken is lowered by the scattered radiation. Usually, in order to remove this scattered radiation, radiography is carried out through a grid constructed by arranging alternately a radiation absorbing layer which uses lead or the like with a high rate of radiation absorption and a radioparent layer which uses aluminum, paper or the like with a low rate of radiation absorption.

However, when an object is radiographed through the grid, a figure with a striped pattern (grid figure) under the influence of the radiation absorbing layers will be superimposed on a radiological image which is a photo image. Conventionally, to reduce this grid figure, there is an oscillating system for oscillating the grid during radiography. However, the apparatus is enlarged by realizing this oscillating system, to give rise to a problem of high cost, for example.

Then, in order to remove the grid figure with variations due to the grid, there is a technique in which, based on sensitivity variations of a plurality of pixels constituting an image sensor, an image for correction for correcting a radiological image of an object under examination is created from image data obtained beforehand through the grid and without the object, and image components due to the grid are removed using the image for correction (see Patent Document 1, for example). In addition, there are techniques of carrying out filtering based on a relationship between grid frequency relating to grids and sampling frequency of image sensors, in order to cope with two or more types of grids and various image sensors (see Patent Documents 2-4, for example).

[Patent Document 1]
Unexamined Patent Publication No. 2005-324069
[Patent Document 2]
U.S. Pat. No. 2,507,659 (pages 1, 3-5, and FIGS. 1-3, 7)
[Patent Document 3]
Unexamined Patent Publication No. 2004-344670 (page 7, FIG. 7, Table 1)
[Patent Document 4]
Unexamined Patent Publication No. 2003-260053 (page 6, Table 1)

DISCLOSURE OF THE INVENTION

Problem to be Solved by the Invention

However, in the case of Patent Document 1 noted above, it is necessary to take an image for correction serving as reference for grid figure removable, beforehand through the grid and without an object under examination as noted above. In fact, it is troublesome, and practically unrealistic, to acquire an image for correction without the object beforehand on each occasion of use. In order to obtain high-precision correction results, it is necessary to ensure that radiographic environments, conditions and so on are in complete agreement between when the image for correction is acquired and when the object is actually radiographed. In many cases, it is practically difficult to have radiographic environments and conditions in complete agreement in actual use situations.

In the case of Patent Document 1 noted above, grid stripe components are selected by spatial filtering from a target image which is the target of correction, on an assumption that grid stripes are steady over the entire image. Since the inclination of the radiation absorbing layers in the grid actually varies with image positions, the frequency bands of the grid stripes may be different between the central portion and peripheral portions of the image, and thus not necessarily steady. Therefore, correction results are low in accuracy since correction is carried out, using the image for correction whose frequency band, actually, is not steady, on the assumption that the frequency band is steady over the entire image. Although variations in sensitivity can be reduced by generating an image for correction beforehand, high-precision correction cannot necessarily be realized since no consideration is made about variations in the accuracy of the correction itself when the image for correction is created.

This invention has been made having regard to the state of the art noted above, and its object is to provide a radiological image processing apparatus and a radiological image processing program which can realize a high-precision correcting process by one radiographic operation without acquiring data for grid correction beforehand.

Means for Solving the Problem

To fulfill the above object, this invention provides the following construction.

A radiological image processing apparatus of this invention is a radiological image processing apparatus for processing a radiological image taken through a grid for removing scattered radiation, comprising a separating device for separating the radiological image into a grid image including components of a grid figure due to the grid and a non-grid image including other components; an adjusting device for adjusting intensity of the grid image on real space based on the non-grid image to generate an adjusted image; and a removing device for subtracting the adjusted image from the non-grid image to generate a corrected image free of influences of the grid.

According to the radiological image processing apparatus of this invention, the separating device separates a radiological image into a grid image including components of a grid figure due to the grid and a non-grid image including other components. Based on the non-grid image, the adjusting device adjusts the intensity of the grid image on real space to generate an adjusted image. Then, the removing device subtracts the adjusted image from the non-grid image to generate a corrected image free of the influence of the grid. Since the corrected image is generated using the radiological image taken through the object under examination, there is no need to take an image for correction beforehand not through the object, and through the grid, for use as a reference for grid figure removal. The images can be acquired from one radiographic operation, without requiring radiographic environments and conditions to be in complete agreement, and with no restrictions, either. The radiological image taken through the object is separated into the grid image and non-grid image, and the intensity of the grid image is adjusted on real space based on the non-grid image to generate a corrected image. Thus, variations of each pixel are taken into account by the adjusted intensity in each pixel of the grid image, to realize a high-precision correcting process. As a result, a high-precision correcting process is realized by one radiographic operation without acquiring data for grid correction beforehand.

One example of the above separating device is arranged to separate the grid image and the non-grid image on a spatial frequency domain. The components of the grid figure and other components can be separated with increased reliability by the separation on the spatial frequency domain. Of course, another example of the separating device may separate the grid image and non-grid image on real space.

Further, the separating device is arranged to separate image components by selecting a periodic pattern in the radiological image. Particularly, since the components of the grid figure often are in a periodic pattern with a frequency band of a certain specific range, it is preferable that the image components are separated by bandpass filter processing which passes through the specific frequency band corresponding to the grid figure. In addition, using the fact that the radiological image with the grid figure superimposed thereon has a periodic pattern on real space, the separating device may separate the image components by selecting components similar to trigonometric functions concerning profiles of intensity on a real space of the radiological image.

When adjusting the intensity of the grid image on the real space based on the non-grid image, the adjusting device adjusts the intensity of the grid image to generate the adjusted image so that components similar to the grid image be excluded from an image obtained by subtracting the adjusted image from the non-grid image. Specifically, the adjusting device is arranged, when a local intensity variation in a grid position of the non-grid image is not monotonic, to adjust the intensity of the grid image to generate the adjusted image so that intensity in a grid position of the grid image become equal to the local intensity variation in the grid position of the non-grid image. Or the adjusting device is arranged to adjust the intensity of the grid image to generate the adjusted image so that intensity in a grid position of the grid image become equal to a difference between intensity in a grid position of the non-grid image and intensity in a grid position of an image obtained by smoothing the non-grid image. By adjusting in this way, components similar to the grid image are not included in the image (i.e. corrected image) obtained by subtracting the adjusted image from the non-grid image, which realizes a still higher-precision correction.

A radiological image processing program of this invention is a radiological image processing program for causing a computer to process a radiological image taken through a grid for removing scattered radiation, comprising a separating step for separating the radiological image into a grid image including components of a grid figure due to the grid and a non-grid image including other components; an adjusting step for adjusting intensity of the grid image on real space based on the non-grid image to generate an adjusted image; and a removing step for subtracting the adjusted image from the non-grid image to generate a corrected image free of influences of the grid; processes in these steps being executed by the computer.

According to the radiological image processing program of this invention, since a corrected image is generated using the radiological image taken through the object under examination, the images can be acquired from one radiographic operation, without acquiring data for grid correction beforehand. The radiological image taken through the object is separated into the grid image and non-grid image, and the intensity of the grid image is adjusted on real space based on the non-grid image to generate a corrected image. Thus, a high-precision correcting process is realized by one radiographic operation.

Effects of the Invention

According to the radiological image processing apparatus and radiological image processing program of this invention, since a corrected image is generated using the radiological image taken through the object under examination, the images can be acquired from one radiographic operation, without acquiring data for grid correction beforehand. The radiological image taken through the object is separated into the grid image and non-grid image, and the intensity of the grid image is adjusted on real space based on the non-grid image to generate a corrected image. Thus, a high-precision correcting process is realized by one radiographic operation.

BRIEF DESCRIPTION OF THE DRAWINGS

FIGS. 3 (a)-(c) are schematic views of images illustrating separation;

FIGS. 5 (a)-(c) are schematic views of profiles illustrating the adjustments.

DESCRIPTION OF REFERENCES

4 . . . image processor
31 . . . grid
41 . . . separating unit
42 . . . adjusting unit
43 . . . removing unit

EMBODIMENT

Figure 1:
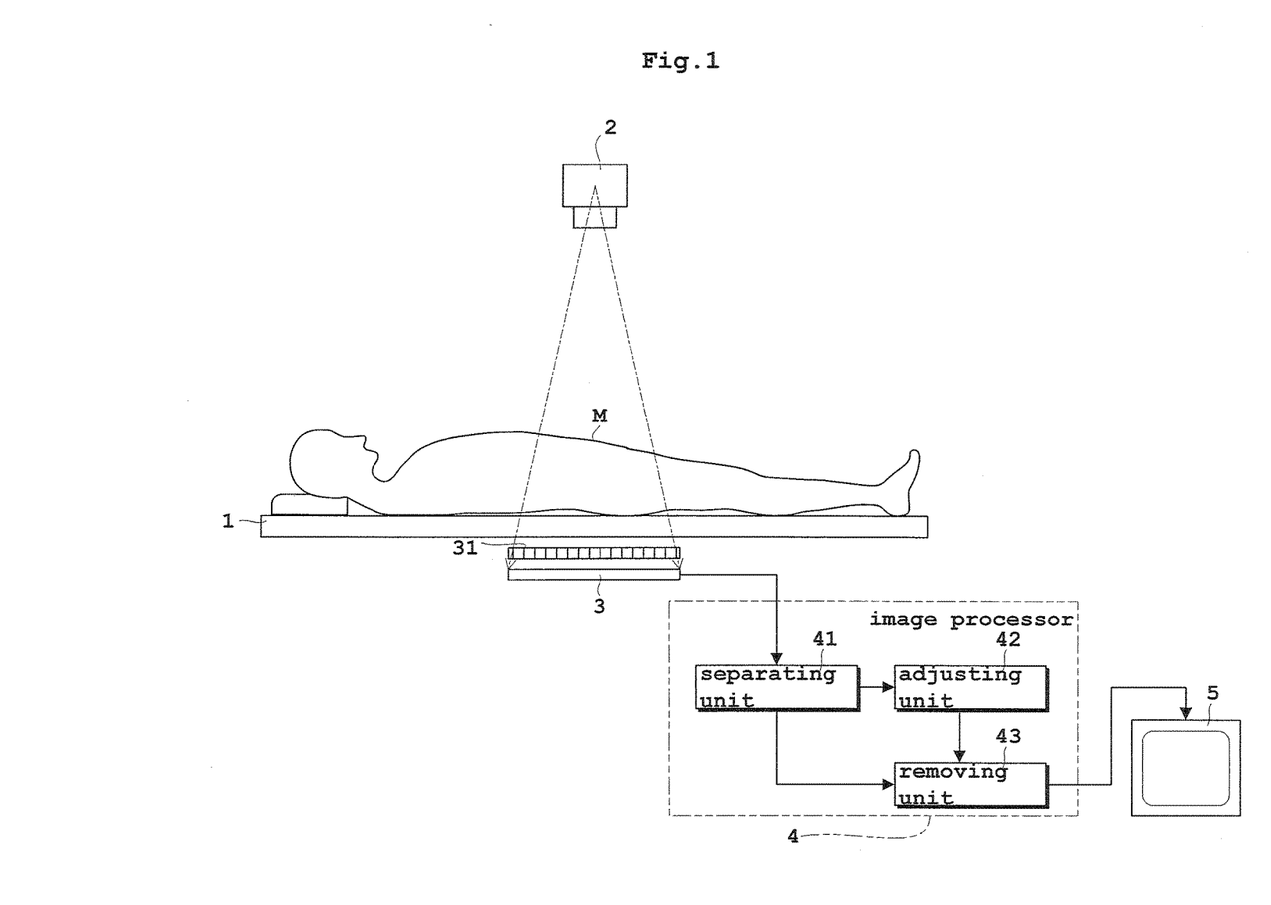
FIG. 1 is a block diagram of a radiological image processing apparatus according to an embodiment.
Figure 2:
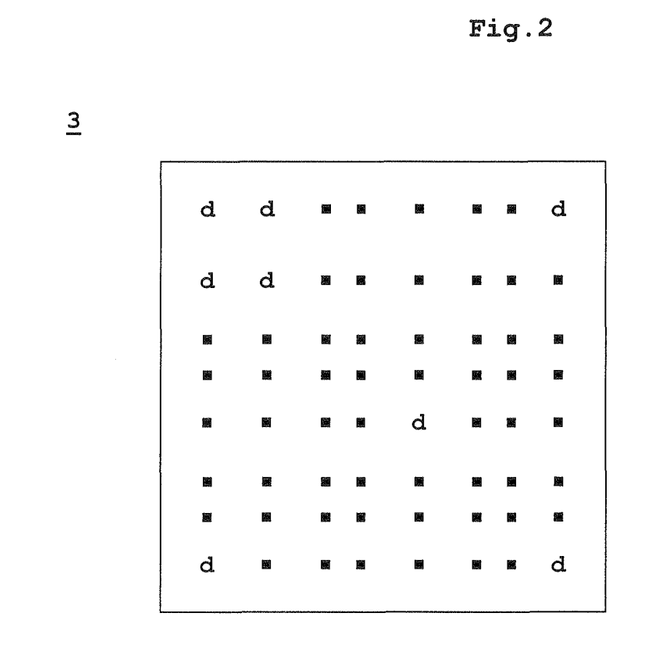
FIG. 2 is a schematic view of a detecting plane of a flat panel radiation detector (FPD)
Figure 4:
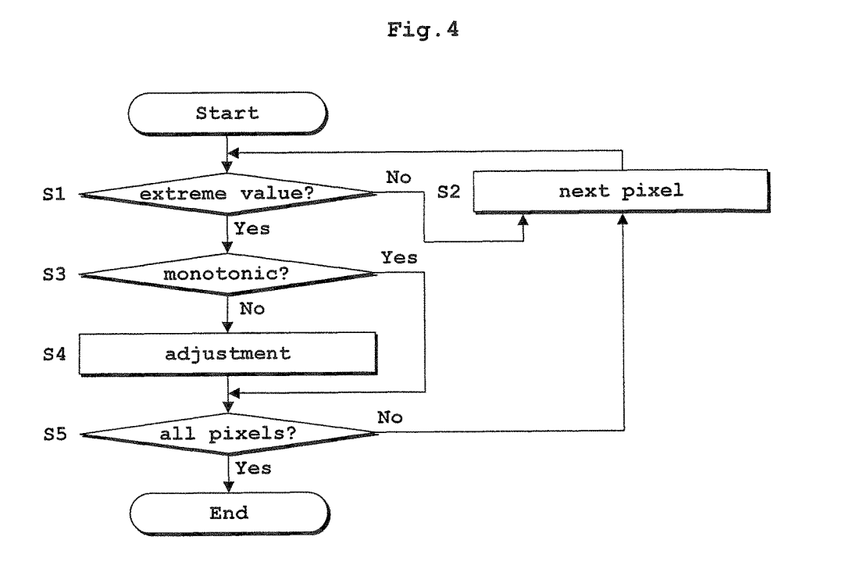
FIG. 4 is a flow chart showing a flow of a series of adjustments.
Figure 5:
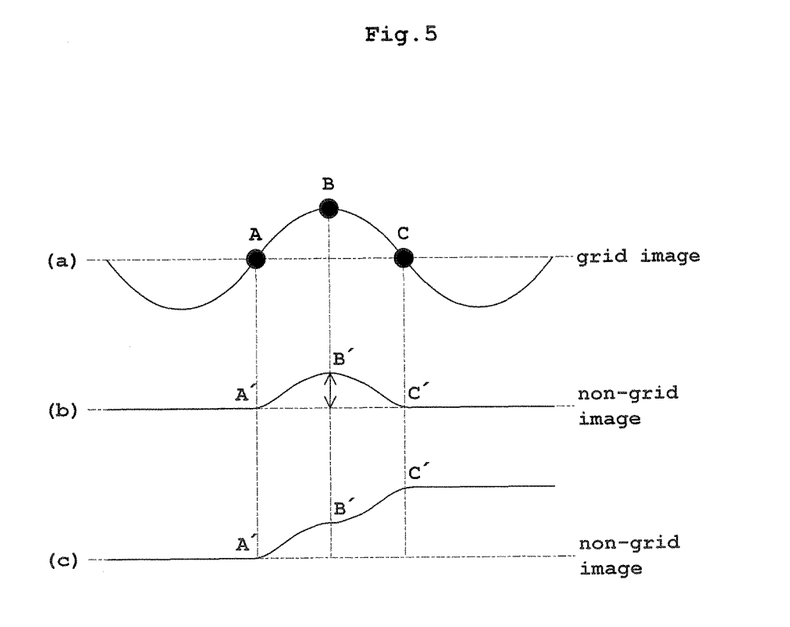

An embodiment of this invention will be described hereinafter with reference to the drawings. FIG. 1 is a block diagram of a radiological image processing apparatus according to the embodiment. FIG. 2 is a schematic view of a detecting plane of a flat panel radiation detector (FPD). FIG. 3 is a schematic view of images illustrating separation. FIG. 4 is a flow chart showing a flow of a series of adjustments. FIG. 5 is a schematic view of profiles illustrating the adjustments.

The radiological image processing apparatus according to this embodiment, as shown in FIG. 1, includes a top board 1 for supporting a patient M, a radiation source 2 (e.g. an X-ray tube) for emitting radiation (e.g. X-rays) toward the patient M, a flat panel radiation detector (hereinafter abbreviated as "FPD") 3 for detecting the radiation emitted from the radiation source 2 and transmitted through the patient M, an image processor 4 for carrying out image processes based on the radiation detected by the FPD 3, and a display 5 for displaying various radiological images having undergone the image processes by the image processor 4. The display 5 is in the form of a display device such as a monitor, television or the like. A grid 31 is attached to the detecting plane of the FPD 3.

The image processor 4 includes a central processing unit (CPU) and others. The programs and the like for carrying out various image processes are written and stored in a storage medium represented by a ROM (Read-only Memory). The CPU of the image processor 4 reads from the storage medium and executes the programs and the like to carry out image processes corresponding to the programs. In particular, a separating unit 41, an adjusting unit 42 and an removing unit 43, described hereinafter, of the image processor 4 execute a program relating to separation of a radiological image, intensity adjustment of a grid image, and removal of the influence of the grid, to carry out separation of the radiological image, intensity adjustment of the grid image and removal of the influence of the grid corresponding to the program, respectively. The program relating to separation of the radiological image, intensity adjustment of the grid image and removal of the influence of the grid corresponds to the radiological image processing program in this invention.

The image processor 4 includes the separating unit 41 which separates a radiological image into a grid image including components of a grid figure due to the grid 31 and a non-grid image including other components, and the adjusting unit 42 which adjusts the intensity of the grid image in real space based on the non-grid image to generate an adjusted image, and the removing unit 43 which subtracts the adjusted image from the non-grid image to generate a corrected image free of the influence of the grid. The separating unit 41 corresponds to the separating device in this invention. The adjusting unit 42 corresponds to the adjusting device in this invention. The removing unit 43 corresponds to the removing device in this invention.

The FPD 3, as shown in FIG. 2, has a plurality of detecting elements d sensitive to radiation arranged in a two-dimensional matrix form on the detecting plane thereof. The detecting elements d detect the radiation by converting the radiation transmitted through the patient M into electronic signals, storing them once, and reading the electric signals stored. The electric signal detected by each detecting element d is converted into a pixel value corresponding to the electric signal. A radiological image is outputted by allotting the pixel values to pixels corresponding to positions of the detecting elements. The radiological image is sent to the separating unit 41 of the image processor 4 (see FIG. 1).

Actual radiography and flows of data relating to each image will be described. By depressing a radiographing button not shown, radiation is generated from the radiation source 2, the radiation is emitted toward the patient M, and radiography is started as interlocked therewith. The radiation generated passes through the patient M, and enters the FPD 3 through the grid 31. The FPD 3 carries out radiography by detecting the radiation and outputting a radiological image. Since the grid 31 is disposed adjacent the detecting plane of the FPD 3 as noted above, the grid 31 removes scattered radiation generated when the radiation is transmitted through the patient M. Therefore, the radiological image outputted from the FPD 3 has the grid figure superimposed thereon due to the influence of the grid 31.

The radiological image with this grid figure superimposed thereon is sent to the separating unit 41 of the image processor 4. The separating unit 41 separates the radiological image into a grid image including components of the grid figure and a non-grid image including other components. This embodiment uses frequency analysis for separating the components. That is, since the components of the grid figure often are in a periodic pattern with a frequency band of a certain specific range, the components are separated by bandpass filter processing which passes through the specific frequency band corresponding to the grid figure.

Where the grid 31 is rated (i.e. a grid designed according to the standard), known grid density $D_g$ of the rated grid 31, and sampling pitch $P_S$ and sampling frequency $f_S$ of the image sensor of the FPD 3 which are also known are used, thereby to derive grid frequency $f_g$ of the grid from the equation: $f_g = P_S \cdot D_g \cdot f_S$. On the other hand, Nyquist frequency $f_n$ is expressed as ½ of sampling frequency $f_S$, i.e. $f_n = f_S/2$. Based on the sampling theorem, if $f_g > f_n$, grid frequency $f_g$ will be the frequency of the grid figure. If $f_g \leq f_n$, $2f_n - f_g$ (i.e. $f_S - f_g$) will be the frequency of the grid figure. And only the frequency of the grid figure is passed by bandpass filter processing. The radiological image is separated into the passed frequency components of the grid figure as the grid image, and remaining frequency components as the non-grid image.

Where the grid 31 is not rated (i.e. not steady over the entire image) but, as noted hereinbefore, the frequency bands of the grid stripes are different between the central portion and peripheral portions of the image, the grid image and non-grid image are separated on the spatial frequency domain instead of using the above sampling theorem. Specifically, the grid image and non-grid image are separated by obtaining a power spectrum from the Fourier transform of the radiological image, and regarding the frequency band of the range where the power spectrum shows a local maximum value as the frequency of the grid figure.

This will be described more particularly. Assuming that the longitudinal and transverse directions of the radiological image are x-direction and y-direction, and that each pixel value is f (x, y), F (μ, v) after the Fourier transform on the spatial frequency domain is expressed by the following equation (1) using f (x, y):

$$F(\mu,v) = \Sigma\Sigma f(x,y) \cdot e^{-j2\pi(\mu_x + v_y)/N} \tag{1}$$

In the above equation (1), j is a complex number, and Σ is a total of y=0 to N−1 and a total of x=0 to N−1.

Figure 3A:
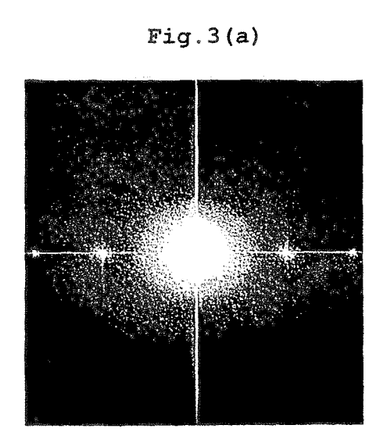
Figure 3B:
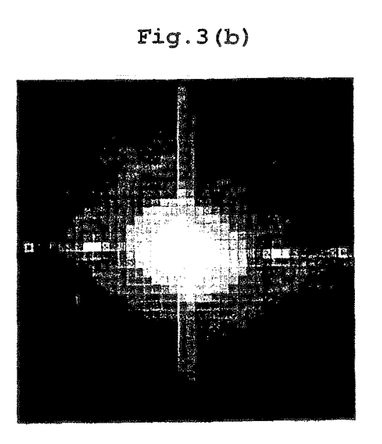
Figure 3C:
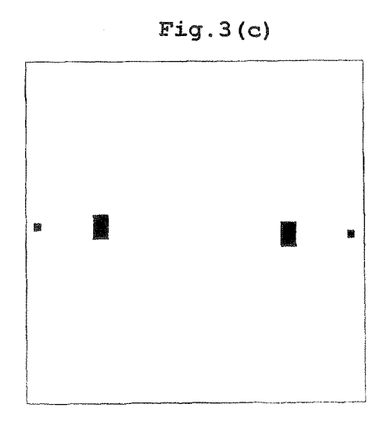

Image F (μ, v) on the spatial frequency domain where the Fourier transform was carried out of the radiological image f (x, y) by the above equation (1) is as shown in FIG. 3 (*a*). That is, FIG. 3 (*a*) shows image F (μ, v) visualizing the power spectrum of radiological image f (x, y). The image in FIG. 3 (*a*) is divided into blocks of a predetermined size set beforehand. FIG. 3 (*b*) shows spectrum data with replacement by average spectral intensity in each block. The spectrum data of FIG. 3 (*b*) is scanned, and results of selection of blocks in positions showing the local maximum value are shown in FIG. 3 (*c*). In FIG. 3 (*c*), the blocks in the positions shown in black in the figure are selected as the local maximum value.

If image F (μ, v) on the spatial frequency domain (after the Fourier transform) is free of the influence of the grid, intensity will decrease monotonically from the image center toward the edges in FIG. 3. If there are locations which take the local maximum value, instead of decreasing monotonically, such locations (blocks) can be considered the frequency band of the grid figure. Therefore, a scan is carried out from the image center in FIG. 3. As does "monotonic" in the intensity adjustment of the grid image described hereinafter, "monotonic" in this specification refers to variations of intensity without taking the extreme value, and intensity varying with the extreme value is considered not "monotonic".

The components having undergone the Fourier transform are separated by bandpass filter processing into components of the frequency band corresponding to the selected block positions (black blocks in FIG. 3 (c)) and components of the frequency band corresponding to the other positions (white portions in FIG. 3 (c)). The grid image and non-grid image are generated by carrying out the inverse Fourier transform to visualize each. f (x, y) after the inverse Fourier transform is expressed by the following equation (2) using F (μ, ν).

$$f(x,y)=\Sigma\Sigma F(\mu,\nu)\cdot e^{j2\pi(\mu_x+\nu_y)/N} \qquad (2)$$

In the above equation (2), Σ is a total of ν=0 to N−1 and a total of μ=0 to N−1.

Thus, where the grid 31 is rated, the frequency of the grid figure is obtained by the sampling theorem, and image components are separated by the bandpass filter processing which passes the frequency of the grid figure. Where the grid 31 is not rated, the grid image and non-grid image are separated on the spatial frequency domain by regarding the frequency corresponding to the block positions where the power spectrum has the local maximum value on the spatial frequency domain by the Fourier transform as frequency of the grid figure, and separating image components by the bandpass filter processing which passes the frequency of the grid figure.

The technique of separation is not limited to the above contents. The grid image and non-grid image may be separated, for example, by separating a frequency band larger than a predetermined value set beforehand and other frequency bands. Instead of being limited to separating the grid image and non-grid image on the spatial frequency domain, the fact that the radiological image with the grid figure superimposed thereon has a periodic pattern on real space may be used, and image components may be separated by selecting components similar to trigonometric functions (e.g. sine waves, cosine waves, products or sums thereof, or other products or sums) concerning profiles of intensity on the real space of the radiological image. That is, using a profile on real space of the radiological image and components similar to trigonometric functions, similar components (extreme value) from a profile (section of the grid figure) perpendicular to the grid figure may be selected, and the selected components may be regarded as a grid image. The frequency analysis also is not limited to the Fourier transform, but a different frequency analysis may be used, such as wavelet transform or Gabor filter. The separation of the radiological image by the separating unit 41 corresponds to the separating step in this invention.

The grid image and non-grid image generated by the separating unit 41 are sent to the adjusting unit 42, and only the non-grid image is sent to the removing unit 43. The adjusting unit 42 adjusts the intensity of the grid image to generate an adjusted image, so that components similar to the grid image may not be included in an image obtained by subtracting the adjusted image described hereinafter from the non-grid image. In this embodiment, the adjusting unit 42 carries out adjustments according to the flow in FIG. 4.

(Step S1) Extreme Value?

The grid image is scanned in the direction perpendicular to the grid figure (sectional direction of the grid figure), to check whether the intensity of an observed pixel indicates a pixel showing the extreme value. Specifically, a comparison is made between the grid image and non-grid image concerning profiles of the intensity perpendicular to the grid figure (section of the grid figure). FIG. 5 (a) shows a profile of the grid image. FIG. 5 (b) shows a profile of the non-grid image in the same position as in FIG. 5 (a) and at a time of not being monotonic. FIG. 5 (c) shows a profile of the non-grid image in the same position as in FIG. 5 (a) and at a time of being monotonic.

(Step S2) Next Pixel

When, in the profile shown in FIG. 5 (a), the intensity of the observed pixel does not indicate a pixel showing the extreme value, attention moves to a next pixel along the direction perpendicular to the grid figure. The operation returns to step S1, and repeats steps S1 and S2 to scan along the direction perpendicular to the grid figure until a pixel showing the extreme value is found.

(Step S3) Monotonic?

When, in the profile shown in FIG. 5 (a), the intensity of the observed pixel indicates a pixel showing the extreme value, it is checked whether the non-grid image varies locally monotonically in a position where intensity shows a local maximum or a local minimum (i.e. grid position of the grid image) as shown in FIG. 5 (a). That is, it is checked whether the local intensity variation in the grid position of the non-grid image is monotonic. Whether the non-grid image varies locally monotonically is determined by comparing the intensities of points corresponding to positions where the local maximum and local minimum of the intensity of the grid image reverse (A and C in FIG. 5 (a)) and an inward position of the extreme value (B in FIG. 5 (a)). Assume that the non-grid images corresponding to points A, B and C of the grid image are A', B' and C' as shown in FIGS. 5 (b) and 5 (c), an average value of the intensity at A' and the intensity at C' is compared with the intensity at B', and when there is a difference exceeding a predetermined range, it is determined not monotonic.

When B' of the non-grid image has the extreme value as shown in FIG. 5 (b), the difference between the average value of the intensity at A' and the intensity at C' and the intensity at B' exceeds the predetermined range, and thus it is determined not monotonic. This intensity at B' is regarded as having the extreme value under the influence of the intensity at B of the grid image. That is, although the non-grid image is separated by the separating unit 41 from the grid image including components of the grid figure, components influenced by the intensity at B of the grid image are, though small in quantity, included in the non-grid image. It can be considered that, because of this, the local intensity variation in the grid position of the non-grid image is not monotonic. When it is not monotonic, the operation proceeds to the following step S4.

Conversely, when B' of the non-grid image does not have the extreme value as shown in FIG. 5 (c), an average value of the intensity at A' with low intensity and the intensity at C' with high intensity, by offset of the intensities at A' and C', becomes such that the intensity is not different from the intensity at B' in the middle. Therefore, the difference between the average value of the intensity at A' and the intensity at C' and the intensity at B' falls within the predetermined range, and thus it is determined monotonic. When it is monotonic, the operation skips the next step S4, and proceeds to the further following step S5.

(Step S4) Adjustment

When the local intensity variation in the grid position of the non-grid image is determined not monotonic in step S3, the intensity of the grid image is adjusted to a fixed multiple so that the intensity in the grid position (i.e. B) of the grid image may become equal to the local intensity variation (difference between the average value of the intensity at A' and the intensity at C', and the intensity at B') in the grid position (i.e. B') of the non-grid image.

(Step S5) all Pixels?

Steps S1-S4 (or steps S1-S3 when monotonic) are carried out about one observed pixel, and it is checked whether all the pixels have been scanned. When all the pixels have been scanned, a series of adjustments is ended noting that all the pixels in the grid image have undergone the intensity adjustment by the adjusting unit 42. When all the pixels have not been scanned, the operation returns to step S1 to repeat steps S1-S4 (or steps S1-S3 when monotonic) for scanning along the direction perpendicular to the grid figure until all the pixels are done.

Thus, the series of adjustments is ended by carrying out steps S1-S5. The technique of adjustment is not limited to the contents described above. Although it is checked whether the local intensity variation in the grid position of the non-grid image is monotonic, as an alternative thereto, the adjusting unit 42 may create an image by smoothing the non-grid image, and the adjusting unit 42 may adjust the intensity of the grid image and generate an adjusted image, so that the intensity in the grid position (B) of the grid image may become equal to a difference between the intensity in the grid position (B') of the non-grid image and the intensity of the grid position of the above smoothed image. The intensity adjustment of the grid image by the adjusting unit 42 corresponds to the adjusting step in this invention.

The adjusted image generated through the adjustment by the adjusting unit 42 is sent to the removing unit 43, while the non-grid image generated by the separating unit 41 as noted hereinbefore is sent to the removing unit 43. The removing unit 43 subtracts the adjusted image from the non-grid image to generate a corrected image free of the influence of the grid. The removal of the influence of the grid by the removing unit 43 corresponds to the removing step in this invention.

The corrected image generated through the removal by the removing unit 43 is sent to the display 5, and the display unit 5 makes a display output of the corrected image. The corrected image generated through the removal by the removing unit 43 may be written and stored in a storage medium represented by a RAM (Random-Access Memory) or the like, to be read as necessary and outputted for printing by a printing device represented by a printer or the like.

According to the radiological image processing apparatus in this embodiment, the separating unit 41 separates a radiological image into a grid image including components of a grid figure due to the grid 31 and a non-grid image including other components. Based on the non-grid image, the adjusting unit 42 adjusts the intensity of the grid image on real space to generate an adjusted image. Then, the removing unit 43 subtracts the adjusted image from the non-grid image to generate a corrected image free of the influence of the grid. Since the corrected image is generated using the radiological image taken through the patient M, there is no need to take an image for correction beforehand through the grid 31 and without the patient M, for use as a reference for grid figure removal. The images can be acquired from one radiographic operation, without requiring environments and conditions in complete agreement, and with no restrictions, either. The radiological image taken through the patient M is separated into the grid image and non-grid image, and the intensity of the grid image is adjusted on real space based on the non-grid image to generate a corrected image. Thus, variations of each pixel (e.g. variations in the sensitivity of the image sensor of FPD 3, and variations of the correction and so on) are taken into account by the adjusted intensity in each pixel of the grid image, to realize a high-precision correcting process. As a result, a high-precision correcting process is realized by one radiographic operation without acquiring data for grid correction beforehand.

In this embodiment, when the grid 31 is not rated, the separating unit 41 separates the grid image and non-grid image on the spatial frequency domain. The components of the grid figure and other components can be separated with increased reliability by the separation on the spatial frequency domain. Of course, the grid image and non-grid image may be separated on real space as noted in the modification which selects components similar to trigonometric functions concerning profiles of intensity on real space of the radiological image.

The separating unit 41 separates image components by selecting a periodic pattern in the radiological image. As noted hereinbefore, since the components of the grid figure often are in a periodic pattern with a frequency band of a certain specific range, it is preferable that the image components are separated by bandpass filter processing which passes through the specific frequency band corresponding to the grid figure.

When the intensity of the grid image is adjusted on real space based on the non-grid image, the adjusting unit 42 adjusts the intensity of the grid image to generate an adjusted image, so that components similar to the grid image may not be included in an image obtained by subtracting the adjusted image from the non-grid image. Specifically, when the local intensity variation in a grid position of the non-grid image is not monotonic, the adjusting unit 42 adjusts the intensity of the grid image to generate an adjusted image so that the intensity in the grid position of the grid image may become equal to the local intensity variation in the grid position of the non-grid image. By adjusting in this way, components similar to the grid image are not included in the image (i.e. corrected image) obtained by subtracting the adjusted image from the non-grid image, which realizes a still higher-precision correction.

This invention is not limited to the foregoing embodiment, but may be modified as follows:

(1) The foregoing embodiment has been described taking X-rays as an example of radiation. However, it is applicable to radiation other than X-rays (such as gamma rays).

(2) In the foregoing embodiment, the radiological image processing apparatus is constructed for medical use to conduct radiography of a patient placed on the top board 1 as shown in FIG. 1. This is not limitative. For example, it may be a construction like a nondestructive testing apparatus for industrial use which conducts radiography of an object (in this case, a subject tested) conveyed on a belt, or a construction like an X-ray CT apparatus for medical use. A radiographic apparatus may be in the form of a separate apparatus as an external apparatus, which apparatus simply includes a separating device, an adjusting device and a removing device.

(3) The grid image appears easily where use is made of an image sensor like a flat panel radiation detector (FPD) having detecting elements arranged to correspond to pixels, respectively. Therefore, where this invention is applied to an FPD, it will be especially useful in that high-precision correction is realized. However, the image sensor is not limited to an FPD. This invention is applicable to any image sensor used generally.

The invention claimed is:

1. A radiological image processing apparatus for processing a radiological image taken through a grid for removing scattered radiation, comprising a separating device for separating the radiological image into a grid image including components of a grid figure due to the grid and a non-grid image including other components: an adjusting device for adjusting intensity of the grid image on real space based on the non-grid image to generate an adjusted image; and a removing device for subtracting the adjusted image from the non-grid image to generate a corrected image free of influences of the grid.

2. The radiological image processing apparatus according to claim 1, wherein the separating device is arranged to separate the grid image and the non-grid image on a spatial frequency domain.

3. The radiological image processing apparatus according to claim 1, wherein the separating device is arranged to separate image components by selecting a periodic pattern in the radiological image.

4. The radiological image processing apparatus according to claim 3, wherein the separating device is arranged to separate the image components by bandpass filter processing which passes through a specific frequency band.

5. The radiological image processing apparatus according to claim 3, wherein the separating device is arranged to separate the image components by selecting components of trigonometric functions concerning profiles of intensity on a real space of the radiological image.

6. The radiological image processing apparatus according to claim 1, wherein the adjusting device is arranged to adjust the intensity of the grid image to generate the adjusted image so that components of the grid image are excluded from an image obtained by subtracting the adjusted image from the non-grid image.

7. The radiological image processing apparatus according to claim 6, wherein the adjusting device is arranged, when a local intensity variation in a grid position of the non-grid image is not monotonic, to adjust the intensity of the grid image to generate the adjusted image so that intensity in a grid position of the grid image become equal to the local intensity variation in the grid position of the non-grid image.

8. The radiological image processing apparatus according to claim 6, wherein the adjusting device is arranged to adjust the intensity of the grid image to generate the adjusted image so that intensity in a grid position of the grid image become equal to a difference between intensity in a grid position of the non-grid image and intensity in a grid position of an image obtained by smoothing the non-grid image.

9. A radiological image processing program for causing a computer to process a radiological image taken through a grid for removing scattered radiation, comprising a separating step for separating the radiological image into a grid image including components of a grid figure due to the grid and a non-grid image including other components; an adjusting step for adjusting intensity of the grid image on real space based on the non-grid image to generate an adjusted image; and a removing step for subtracting the adjusted image from the non-grid image to generate a corrected image free of influences of the grid; processes in these steps being executed by the computer.

10. The radiological image processing apparatus according to claim 5, wherein the components of trigonometric functions are sine waves, cosine waves, products or sums thereof, or other products or sums.

* * * * *